United States Patent [19]

Elango et al.

[11] Patent Number: 5,008,439

[45] Date of Patent: Apr. 16, 1991

[54] SYNTHESIS OF 2-(4-HYDROXYPHENOXY) ALKANOIC ACID ESTERS

[75] Inventors: Varadaraj Elango; Kenneth G. Davenport, both of Corpus Christi, Tex.

[73] Assignee: Hoechst Celanese Corporation, North Somerville, N.J.

[21] Appl. No.: 170,711

[22] Filed: Mar. 21, 1988

[51] Int. Cl.$^5$ .............................................. C07C 69/76
[52] U.S. Cl. .................................... 560/61; 558/414; 560/62; 260/410.5
[58] Field of Search .................. 560/61; 558/414; 180/62; 260/410.5

[56] References Cited

U.S. PATENT DOCUMENTS

| | | | |
|---|---|---|---|
| 2,068,905 | 1/1937 | Bruson | 260/112 |
| 2,449,993 | 9/1948 | Gresham et al. | 562/470 |
| 3,413,341 | 11/1968 | Bursack et al. | 562/471 |
| 3,968,143 | 7/1976 | Schacht et al. | 560/61 |
| 3,976,702 | 8/1976 | Suzuki et al. | 560/61 |
| 4,035,416 | 7/1977 | Brust | 562/471 |
| 4,051,318 | 9/1977 | Suzuki et al. | 560/131 |
| 4,130,413 | 12/1978 | Handte . | |
| 4,153,803 | 5/1979 | Thiele et al. | 560/57 |
| 4,169,720 | 10/1979 | Schacht et al. | 71/108 |
| 4,173,709 | 11/1979 | Metivier et al. | 562/471 |
| 4,174,460 | 11/1979 | Seifert et al. | 568/629 |
| 4,528,394 | 7/1985 | Otterbacher . | |
| 4,532,346 | 7/1985 | Rehn . | |
| 4,532,346 | 7/1985 | Rehn et al. | 562/471 |
| 4,537,984 | 8/1985 | Hashiba et al. | 560/61 |
| 4,547,583 | 10/1985 | Nestler | 560/61 |
| 4,568,497 | 2/1986 | Mendoza et al. | 562/471 |
| 4,661,505 | 4/1987 | Marshall et al. . | |
| 4,665,212 | 5/1987 | Makino et al. | 562/471 |
| 4,739,101 | 4/1988 | Bourgogne | 560/61 |
| 4,747,865 | 5/1988 | Shiokawa . | |

FOREIGN PATENT DOCUMENTS

| | | |
|---|---|---|
| 0082413 | 8/1982 | European Pat. Off. . |
| 178929 | 4/1986 | European Pat. Off. . |
| 2003430 | 8/1969 | Fed. Rep. of Germany . |
| 55-79344 | 6/1980 | Japan . |
| 1599121 | 9/1961 | United Kingdom . |

OTHER PUBLICATIONS

C.A. 108(1):5692k, 1987.
C.A. 77(13):88107p, 1971.
Ogata, Y.,(1987), J. Org. Chem., 43(12), pp. 2417–2419.
McKillop, A., (1987), Tetrahedron, 43(8), pp. 1753–1758.

*Primary Examiner*—Paul J. Killos
*Attorney, Agent, or Firm*—Richard S. Roberts; Shirley L. Church

[57] ABSTRACT

A method for synthesizing 2-(4-hydroxyphenoxy)alkanoic acid esters by reacting a hydroxyaromatic ketone derivative with a 2-substituted alkanoic acid ester under basic conditions and thereafter oxidizing the intermediate with subsequent hydrolysis.

25 Claims, No Drawings

SYNTHESIS OF 2-(4-HYDROXYPHENOXY) ALKANOIC ACID ESTERS

BACKGROUND OF THE INVENTION

The present invention relates to a method for the synthesis of 2-(4-hydroxyphenoxy)alkanoic acid esters. Such compounds are useful in the production of herbicides and dyes.

It is known in the art to produce herbicidal agents which are of the 2-(aryloxyphenoxy)alkanoic acid class. Within this context aryl includes phenyl, pyridyl, benzoxazolyl, etc.

These and other compounds are more fully described in U.S. Pat. Nos. 4,589,908; 4,130,413; 4,391,995; 4,301,295; 4,238,626; 3,784,697; 3,721,703; and 3,954,442; 4,657,577; 4,046,553; 4,629,493; and 4,368,068, all of which are incorporated herein by reference.

The production of these herbicides requires the use of an intermediate which is a 2-(4-hydroxyphenoxy)-alkanoic acid ester (I) of the formula:

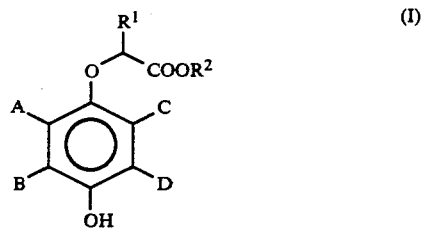

wherein the variables are hereinafter defined.

However, prior processes for producing these intermediate compounds have employed hydroquinone and other compounds as starting materials. Mono-o-alkylation of hydroquinone is achieved by using a large excess of hydroquinone, but this method warrants low conversion. Alternatively, one can make mono-o-protected hydroquinone, alkylate, and remove the protecting group. However, the cost of such a manufacturing procedure is very large. Mono-o-alkylated hydroquinone derivatives, such as 2-(4-hydroxyphenoxy)propanoic acid are difficult to obtain because both of the hydroxyl groups of hydroquinone tend to react with the alkylating agent. Such processes are discussed at length in U.S. Pat. Nos. 3,600,437; 4,532,346; 4,547,583; 4,613,677; 4,489,207; and 4,368,068 and British Patent 1,591,063. U.S. Pat. No. 4,665,212 teaches condensed hydroquinone or hydroquinone salts with certain aromatic sulfonyl containing acids, esters and salts. U.S. Pat. No. 4,511,731 teaches the preparation of certain propanoate monoethers of hydroquinone via sequential alkylation and oxidation of hydroxystyrene. While such processes are effective for producing herbicide precursors, they are economically disadvantageous since the rate of conversion and selectivity, and hence the yield, is relatively low; on the order of about 10%. U.S. Pat. No. 4,528,394 describes a method which improves upon this yield by using a benzaldehyde precursor, such that the yield is increased to about 50%. However, this system is disadvantageous because of the vigorous reaction conditions required and undesired side reactions which occur such as the self-condensation of the benzaldehyde. These may also undergo undesired oxidation to carboxylic acids under Baeyer-Villiger conditions. The present invention improves on these methods by preparing intermediates derived from certain ketones and conducting a Baeyer-Villager oxidation thereon. The intermediates are prepared in a stepwise fashion and several advantages are thereby noted. These include a higher yield, perhaps in the 80–95% range, easier purification of the intermediates and less vigorous reaction conditions.

SUMMARY OF THE INVENTION

The invention provides a method for synthesizing 2-(4-hydroxyphenoxy)alkanoic acid esters which comprises reacting a hydroxyaromatic ketone derivative (II) of the formula

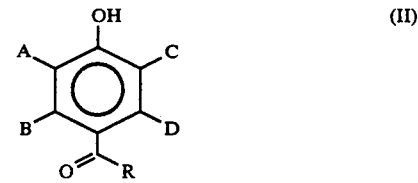

or a salt thereof; with a substituted ester of the formula

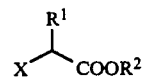

under basic conditions to thereby form a 2-(acylphenoxy)alkanoic acid ester (III) of the formula

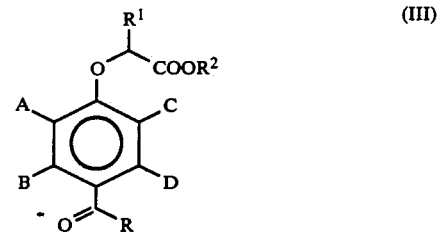

and then oxidizing the thusly formed 2-(acylphenoxyl)alkanoic acid ester (III) with a peracid or peroxide to obtain a 2-(acyloxyphenoxy)alkanoic acid ester of the formula (IV)

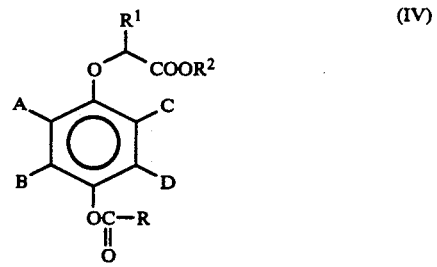

and then hydrolyzing or alcoholizing acid 2-(acyloxyphenoxy)alkanoic acid ester with $R^3OH/H^+$ to obtain a 2-(4-hydroxyphenoxy)alkanoic acid ester of the formula (I)

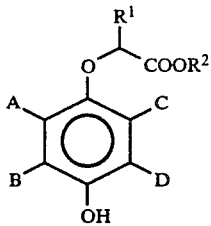

(I)

wherein R is $C_1$ to $C_{18}$ alkyl or $C_6$ to $C_{10}$ aryl, preferably $C_1$ to $C_4$ alkyl, and most preferably methyl; and wherein $R^1$ is H, phenyl or $C_1$ to $C_{18}$ alkyl, preferably $C_1$ to $C_4$ alkyl and most preferably H or methyl; and wherein $R^2$ and $R^3$ are independently $C_1$ to $C_{18}$ alkyl, preferably $C_1$ to $C_4$ alkyl or aryl such as phenyl or naphthyl which may be substituted or unsubstituted; and wherein A, B, C and D are independently H, X, CN, $C_1$ to $C_{18}$ alkyl, or $C_6$ to $C_{10}$ aryl, protected using methods well-known to those skilled in the art so to avoid reaction of said substituents under the conditions of the process, i.e., alkylation, oxidation, solvolysis; and X is F, Cl, Br, I or a sulfonic ester. It must however be noted that the invention is not limited to 4-substituted isomers of 2-(acylphenoxy)alkanoic acid esters but also contemplates 2- and 3-substituted 2-(acylphenoxy)alkanoic acid esters.

DETAILED DESCRIPTION OF THE PREFERRED EMBODIMENT

In the production of the 2-(4-hydroxyphenoxy)alkanoic acid esters (I) of this invention, one begins with a hydroxyaromatic ketone (II) and reacts it with one of the aforesaid substituted esters under basic conditions. This reaction product is then subjected to a Baeyer-Villiger oxidation with peracetic acid being the preferred reagent. The resulting product is then hydrolyzed or alcoholized to afford the desired 2-(4-hydroxyphenoxy)alkanoic acid esters (I). The reaction sequence may be generalized as:

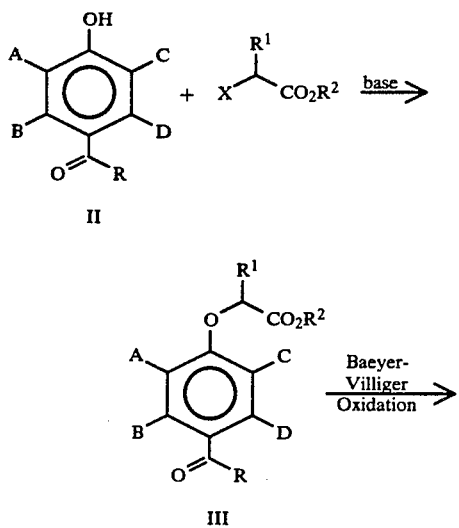

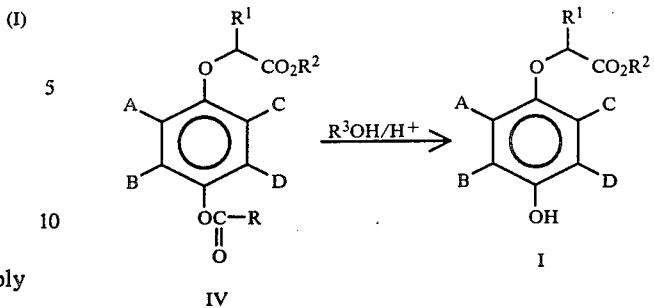

The compounds of the formulae I, III, and IV possess an asymmetric carbon center and can therefore occur as pure enantiomers (optically active) or racemic as mixtures of enantiomers. An important feature of this invention is to begin the synthesis with an aromatic ketone which is specifically a 4-hydroxyphenyl ketone compound (II). The most preferred ketone being 4-hydroxyacetophenone, as well as its sodium or potassium salts. These hydroxyaromatic ketones are then reacted with one of the aforesaid X-substituted esters which may be either racemic or optically active. Preferred esters are halogen substituted propanoates such as methyl 2-chloropropanoate, methyl 2-bromopropanoate, ethyl 2-chloropropanoate, ethyl 2-[(methylsulfonyl)oxy]propanoate and ethyl 2-[(toluylsulfonyl)oxy]propanoate. This reaction proceeds by the Williamson's ether synthesis which is well-known to the skilled artisan. The reaction may take place by refluxing the hydroxyaromatic ketone with the ester in a solvent such as dimethylformamide under basic conditions. The basic conditions may be provided either by direct use of a base such as an alkali metal or alkaline earth metal hydroxide or carbonate, amines or a hydride such as sodium hydride. Alternatively, within the meaning of this invention, the basic media may be provided by using one of the aforesaid salt forms of the hydroxyaromatic ketone, such as 4-hydroxyacetophenone sodium or potassium salt. Alternative solvents for the refluxing reaction non-exclusively include polar protic solvents, e.g., water, or alcohol; or polar aprotic solvents, e.g., ketones, ethers, nitriles, and sulfoxides. The reaction may take place at from about 0.1 to about 72 hours, or more preferably from about 1 to about 48 hours at a temperature of from about 0° C. to about 300° C. or more preferably from about 25° C. to about 200° C. The reaction product of this juncture is a 2-(acylphenoxy)alkanoic acid ester (III). In one preferred embodiment the foregoing reactants are 4-hydroxyacetophenone potassium salt and ethyl 2-chloropropanoate with refluxing in dimethylformamide. Alternatively, the reactants are 4-hydroxyacetophenone, potassium hydroxide and ethyl 2-chloropropanoate with refluxing in dimethylformamide. Therefore the preferred 2-(acylphenoxy)alkanoic acid ester produced is ethyl 2-(4-acetylphenoxy)propanoate. This is then oxidized by the Baeyer-Villiger oxidation process which is also well-known to the skilled artisan per se. The oxidation is conducted by refluxing the 2-(acylphenoxy)alkanoic acid ester with a peracid or peroxide in a suitable solvent. The most preferred oxidizing agent is peracetic acid. Others nonexclusively include hydrogen peroxide, alkyl peroxides, chloroperacetic acid, peroxybenzoic acid, meta-chloroperoxybenzoic acid and trifluoroperoxyacetic acid. One preferred solvent for the refluxing is acetic acid. Alternative solvents for the refluxing reaction non-exclusively include water, alcohols, esters, ethers, halogenated hydrocarbons and carboxylic acids. The reaction may take place at from about 0.01 to about 24 hours, or more preferably from about 0.1 to about 10 hours at a temperature of from about 0° C. to about 100° C. or more preferably from about 25° C. to about 75° C. The reaction may take place at either elevated or reduced pressures, however, preferably it is performed at reduced pressure to remove heat generated during the reaction.

The reaction product of this juncture is a 2-(acyloxyphenoxy)alkanoic acid ester which in the most preferred embodiment is alkyl 2-(4-acetoxyphenoxy)-propanoate. This latter component is then hydrolyzed or alcoholized. The alcoholysis may be conducted by contacting with alcohols under acidic conditions and elevated temperatures for a period of time sufficient to permit the reaction to approach completion. The amount of alcohol used may be, for example, about 0.5 to about 1,000 mol equivalents, preferably about 1 to about 100 mol equivalents based on the ester being alcoholized. The acids which may be employed for this purpose are organic acids such as methanesulfonic acid, para-toluenesulfonic acid, mineral acids such as sulfuric, hydrochloric and phosphoric acids, and acidic ion exchange resins. In some instances, it may be desirable to employ a combination of alcohol and water to achieve a measure of solvolysis.

Alcoholysis may take place at from about 0.1 to about 10 hours, or more preferably from about 0.5 to about 4 hours at a temperature of from about 20° C. to about 200° C. or more preferably from about 60° C. to about 140° C. The reaction is conducted with an anticipated conversion of from about 90% to about 99% with a selectivity of from about 90% to about 98%. The solvolysis product is a 2-(4-hydroxyphenoxy)alkanoic acid ester which in the preferred embodiment is alkyl 2-(4-hydroxyphenyl)propanoate. The alcoholysis process of this invention provides for the recovery of the phenolic product in relatively higher yields. The product may be recovered by conventional purification methods usually involving a combination of crystallization, filtration, washing and distillation in any order deemed advantageous for the system at hand.

The following non-limiting examples serve to illustrate the invention.

EXAMPLE 1

To a solution of 4-hydroxyacetophenone potassium salt (8.8g, 500 mmol) in methanol (50 mL) is added methyl 2-bromopropanoate (11.08, 65.0 mmol) dropwise over 30 minutes under nitrogen. The mixture is refluxed under nitrogen for 24 hours during which KBr is accumulated. The reaction is monitored by thin layer chromatography using 100% ethyl acetate. The reaction is cooled to room temperature and the KBr is filtered out. Ethyl acetate (50 mL) is added to give a turbid solution which is refiltered. The reaction product is analyzed by GLC and found to yield methyl 2-(4-acetylphenoxy)propanoate (13.2 g). (m.p. 54.8° C.); IR (KBr) 1757.7 (vs), 1666.8 (vs); $^1$H NMR (CDCl$_3$) delta 1.54 (d, J=6.8 Hz, 3H), 2.42 (s, 3H), 3.64 (s, 3H), 4.76 (q, J=6.8 Hz, 1H), 6.79 and 7.80 (dd, J=8.0 Hz, 4H).

EXAMPLE 2

To a solution of the potassium salt of 4-hydroxyacetophenone (25.0 g, 0.14 mol) in dimethylformamide (DMF) (100 mL) is added methyl 2-chloropropanoate (24.5 g, 0.20 mol) over 30 minutes and stirred at 85–90° C. for 3 hours under nitrogen. The reaction is filtered to remove KCl and the filtrate is concentrated under reduced pressure to remove DMF and the product analyzed by GLC. The product is dissolved in ethyl acetate (300 mL) and extracted with 2N NaOH (2×100 mL) and water (100 mL). The organic phase is dried and concentrated to give pure methyl 2-(4-acetylphenoxy)-propanoate (25 g) (yield 64%).

EXAMPLE 3

To a solution of the potassium salt of 4-hydroxyacetophenone (25.0 g, 0.14 mol) in DMF (100 mL) is added ethyl 2-chloropropanoate (27.3 g, 0.20 mol) over 30 minutes and stirred at 85–90° C. for 3 hours under nitrogen. The reaction is filtered to remove KCl and the filtrate is concentrated under reduced pressure to remove DMF and the product is analyzed by GLC. The product is dissolved in ethyl acetate (300 mL) and extracted with 2N NaOH (2×100 mL) and water (100 mL). The organic phase is dried and concentrated to give pure ethyl 2-(4-acetylphenoxy)-propanoate (30 g) (yield 75%); m.p. 49.6° C.; IR (KBr) 1747.7 (vs), 1669.8 (vs); $^1$H NMR (CDCl$_3$) delta 1.18 (t, J=7.2 Hz, 3H), 1.58 (d, J=6.8 Hz, 3H), 2.46 (s, 3H), 4.15 (q, J=7.2, 2H), 4.77 (q, J=6.8, 1H), 6.83 and 7.84 (dd, J=9.0 Hz, 4H).

EXAMPLE 4

A solution of the potassium salt of 4-hydroxyacetophenone (17.6 g, 0.1 mol) in DMF (50 mL) is added to a solution of ethyl L-2-[(methylsulfonyl)oxy]-propanoate (21.5 g, 0.11 mol) in DMF (40 mL) over 15 minutes at 80° C. and stirred at 80° C. for 2 hours. To the reaction is added ethyl acetate (100 mL) and filtered. The filtrate is concentrated under reduced pressure whereupon the product is analyzed by GLC. The product is dissolved in ethyl acetate (250 mL) and extracted with saturated sodium bicarbonate solution (2×100 mL) and water (2×60 mL). The organic phase is dried and concentrated to give ethyl 2-(4-acetylphenoxy)propanoate (20.2 g).

EXAMPLE 5

To a solution of methyl 2-(4-acetylphenoxy)propanoate (5.6g, 25.0 mmol) in acetic acid (25 mL) is added peracetic acid (35%, 6.5g, 30.0 mmol) dropwise over 30 minutes at 25° C. The reaction is refluxed at 70° C. for 5 hours to give an orange-brown liquid. Acetic acid and residual peracetic acid are removed by high vacuum. The solution is kugelrohr distilled to give a light brown-orange product which contains methyl 2-(4-acetoxyphenoxy)propanoate (conversion 93%, selectivity 76%, yield 71%) and methyl 2-(4-hydroxyphenoxy)propanoate.

EXAMPLE 6

Methyl 2-(4-acetylphenoxy)propanoate (22.4 g, 100.0 mL) is dissolved in acetic acid (100 mL). Purified peracetic acid (19%, 58.0 g, 145.0 mmol) is dropwise added to the reaction at 58° C. and 60 mmHgA. The reaction is refluxed for 10 hours at 58° C. and 60 mm HgA whereupon the reaction is analyzed by GLC. The reaction is cooled to room temperature and concentrated under reduced pressure to give pure methyl 2-(4-acetoxyphenoxy)propanoate (20.13 g) (yield 84%):b.p 96–98° C. at 0.15 mm HgA, IR(neat) 1757.8 (vs); $^1$H NMR (CDCl$_3$) delta 1.58 (d, J=6.9 Hz, 3H), 2.23 (s, 3H), 3.72

(s, 3H), 4.70 (q, J=6.9 Hz, 3H), 6.84 and 6.96 (dd, J=9.2 Hz, 4H).

EXAMPLE 7

To a solution of ethyl 2-(4-acetylphenoxy)propanoate (5.01 g, 21.0 mmol) in equilibrium with acetic acid (50 mL) is added peracetic acid (16%, 15.61 g, 33.0 mmol) dropwise over 30 minutes at 58° C. and 60 mm HgA until all is added. The reaction mixture is refluxed at a temperature of 48°-54° C. and a vacuum of 55-60 mm Hg. The reaction continues for 8 hours, is cooled to room temperature and concentrated under reduced pressure to remove the acetic acid from which ethyl 2-(4-acetoxyphenyl)propanoate (5.34 g) is obtained. (yield 90%):b.p. 120-122° C. at 0.06 mm HgA, IR (neat) 1752 (vs); $^1$H NMR (CDCl$_3$) delta 1.22 (t, J=7.0 Hz, 3H), 1.57 (d, J=6.8 Hz, 3H), 2.23 (s, 3H), 4.18 (q, J=7.0 Hz, 2H), 4.70 (q, J=6.8 Hz, 1H), 6.85 and 6.96 (dd, J=9.4 Hz, 4H).

EXAMPLE 8

Ethyl 2-(4-acetylphenoxy)propanoate (5.01 g, 21.0 mmol) is dissolved in acetic acid (10 mL) and Amberlyst-15$^{(R)}$ (0.24 g) added. Hydrogen peroxide (70%), 1.58 g, 33.0 mmol) is then charged dropwise over 30 minutes to the reaction. The reaction is refluxed for 8 hours at 45-60° C. and 57-60 mm HgA whereupon the reaction is analyzed by GLC. The reaction is cooled to room temperature and concentrated under reduced pressure to give ethyl 2-(4-acetoxyphenoxy)propanoate (4.72 g) (yield 88.3%).

EXAMPLE 9

Methyl 2-(4-acetoxyphenoxy)propanoate (1.0 g, 4.2 mmol) is hydrolyzed by refluxing for 2 hours at 80° C. with methanol (10 mL) and concentrated HCL (36%, 2 drops). The reaction product is concentrated under reduced pressure to obtain methyl 2-(4-hydroxyphenoxy)propanoate (0.81 g). Conversion 99%, selectivity 99%, yield 97%; IR (neat) 1757 (vs) $^1$H NMR (CDCl$_3$) delta 1.60 (d, J=7.0 Hz, 3H), 3.80 (s, 3H), 4.85 (q, J=7.0 Hz, 1H), 6.82 (s, 4H).

What is claimed is:

1. A method for synthesizing 2-(4-hydroxyphenoxy)alkanoic acid esters which comprises reacting a hydroxyaromatic ketone derivative (II) of the formula

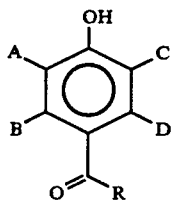

or a salt thereof; with a substituted ester of the formula

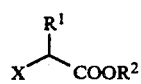

under basic conditions to thereby form a 2-(acylphenoxy)alkanoic acid ester (III) of the formula

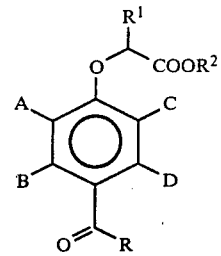

and then oxidizing the thusly formed 2-(acylphenoxy)alkanoic acid ester with a peracid or peroxide to obtain a 2-(acyloxyphenoxy)alkanoic acid ester (IV) of the formula

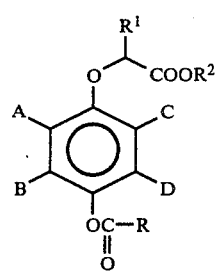

and then transesterifying said 2-(acyloxyphenoxy)alkanoic acid ester with R$^3$OH/H$^+$ to obtain a 2-(4-hydroxyphenoxy)alkanoic acid ester (I) of the formula

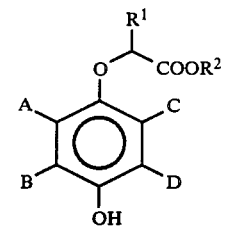

wherein R is C$_1$ to C$_{18}$ alkyl or C$_6$ to C$_{10}$ aryl; and
wherein R$^1$ is H, phenyl or C$_1$ to C$_{18}$ alkyl; and
wherein R$^2$ and R$^3$ are independently C$_1$ to C$_{18}$ alkyl or aryl; and
wherein A, B, C and D are independently H, X, CN, C$_1$ to C$_{18}$ alkyl, or C$_6$ to C$_{10}$ aryl; and X is F, Cl, Br, I or a sulfonic ester.

2. The method of claim 1 wherein A, B, C and D are hydrogen.

3. The method of claim 1 wherein R is CH$_3$.

4. The method of claim 1 wherein said hydroxyaromatic ketone is a potassium or sodium salt.

5. The method of claim 1 wherein R$^1$ is CH$_3$.

6. The method of claim 1 wherein R$^2$ is CH$_3$, C$_2$H$_5$, or C$_4$H$_9$.

7. The method of claim 1 wherein X is bromine, chlorine, mesylate, or tosylate.

8. The method of claim 1 wherein R$^1$ is CH$_3$, R$_2$ is CH$_3$, C$_2$H$_5$, or C$_4$H$_9$ and X is bromine.

9. The method of claim 1 wherein said base is sodium hydroxide or potassium carbonate.

10. The method of claim 1 wherein said base is selected from the groups consisting of alkali metal and alkaline earth metal hydroxides or carbonates, amines and hydrides.

11. The method of claim 1 wherein $R^2$ is alkyl.

12. The method of claim 1 wherein said oxidation is conducted with peracetic acid.

13. The method of claim 1 wherein oxidation is conducted with a compound selected from the group consisting of chloroperacetic acid, peroxybenzoic acid, trifluoroperoxyacetic acid, meta-chloroperoxybenzoic acid, an alkyl peroxide or hydrogen peroxide.

14. The method of claim 1 wherein said alcoholysis is conducted with an alcohol, an ion exchange resin or an acid.

15. The method of claim 1 wherein said transesterification is conducted with hydrochloric acid.

16. The method of claim 5 wherein R is methyl.

17. The method of claim 16 wherein A, B, C and D are hydrogen.

18. The method of claim 16 wherein X is bromine and $R^2$ is $CH_3$, $C_2H_5$, or $C_4H_9$.

19. The method of claim 1 wherein A, B, C and D are hydrogen, R is $CH_3$ and the oxidation is conducted with peracetic acid.

20. The method of claim 19 wherein $R^1$ is hydrogen or $CH_3$, X is halo, $R^2$ is $CH_3$, $C_2H_5$, $C_4H_9$, and the hydrolysis is conducted with an alcohol and an acid.

21. The method of claim 1 wherein said substituted ester is an optically active compound.

22. The compounds 2-(acyloxyphenoxy)alkanoic acid esters of the formula

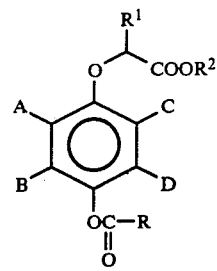

wherein R is $C_1$ to $C_{18}$ alkyl or $C_6$ to $C_{10}$ aryl; and wherein
$R^1$ is H, phenyl or $C_1$ to $C_{18}$ alkyl; and
wherein $R^2$ and $R^3$ are independently $C_1$-$C_{18}$ alkyl or aryl; and
wherein A, B, C and D are independently H, X, CN, $C_1$ to $C_{18}$ alkyl, or $C_6$ to $C_{10}$ aryl; and X is F, Cl, Br, I or a sulfonic ester.

23. The compound methyl 2-(4-acetoxyphenoxy)-propanoate.

24. The compound ethyl 2-(4-acetoxyphenoxy)-propanoate.

25. The compound n-butyl 2-(4-acetoxyphenoxy)-propanoate.

* * * * *